(12) United States Patent
Kim

(10) Patent No.: US 10,617,370 B2
(45) Date of Patent: Apr. 14, 2020

(54) X-RAY APPARATUS AND CONTROL METHOD FOR THE SAME

(71) Applicant: Samsung Electronics Co., Ltd., Suwon-si, Gyeonggi-do (KR)

(72) Inventor: Myeong Je Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 92 days.

(21) Appl. No.: 16/025,819

(22) Filed: Jul. 2, 2018

(65) Prior Publication Data
US 2018/0317863 A1 Nov. 8, 2018

Related U.S. Application Data

(63) Continuation of application No. 15/371,089, filed on Dec. 6, 2016, now Pat. No. 10,028,710.

(30) Foreign Application Priority Data

Mar. 17, 2016 (KR) .................. 10-2016-0032143

(51) Int. Cl.
A61B 6/00 (2006.01)
A61B 6/10 (2006.01)

(52) U.S. Cl.
CPC ............ *A61B 6/105* (2013.01); *A61B 6/4405* (2013.01); *A61B 6/467* (2013.01)

(58) Field of Classification Search
CPC .................................................. A61B 6/4405
See application file for complete search history.

(56) References Cited

U.S. PATENT DOCUMENTS

2013/0064351 A1* 3/2013 Urbon .................. A61B 6/56
378/98.5

* cited by examiner

Primary Examiner — Dani Fox

(57) ABSTRACT

An X-ray apparatus capable of releasing a locked rotation of a wheel using a power supplied from an auxiliary battery of an X-ray detector when a body is discharged, and a control method thereof. A mobile X-ray apparatus includes a body including a body battery, a detector accommodator and a wheel, an X-ray source emits X-rays to an object, a detector battery connector provided on the body and connectable to a detector battery, a power supply circuit connected to the detector battery connector to form a first path in which a power is supplied from the body battery to the detector battery and a second path in which a power is supplied from the detector battery to the body, and a controller controls the power supply circuit to selectively form the first path and the second path.

20 Claims, 16 Drawing Sheets

X-RAY APPARATUS AND CONTROL METHOD FOR THE SAME

CROSS-REFERENCE TO RELATED APPLICATION(S) AND CLAIM OF PRIORITY

The present application is a continuation of U.S. application Ser. No. 15/371,089, filed Dec. 6, 2016, which is related to and claims priority to Korean Patent Application No. 10-2016-0032143, filed on Mar. 17, 2016 in the Korean Intellectual Property Office, the disclosure of which is incorporated herein by reference.

BACKGROUND

1. Field

Embodiments of the present disclosure relate to an X-ray apparatus having a wheel to allow the X-ray apparatus to be movable and a control method of the same.

2. Description of Related Art

Generally, a medical imaging apparatus is an apparatus to provide an image by acquiring information of a patient. The medical imaging apparatus includes an X-ray apparatus, an ultrasonic diagnosis apparatus, a computed tomography (CT) apparatus and a magnetic resonance imaging (MRI) apparatus.

Among this, the X-ray apparatus is a noninvasive diagnosis apparatus capable of imaging an inner structure of an object by emitting X-rays to the object and detecting the penetrated X-rays.

In a conventional X-ray apparatus, because an X-ray source and an X-ray detector are fixed to a certain space, a patient should move to an examination room in which the X-ray imaging apparatus is placed, and the patient may be needed to place his/her body to fit the X-ray imaging apparatus.

However, there may be a difficulty in scanning a patient having movement difficulties with a conventional X-ray imaging apparatus, and thus a mobile X-ray apparatus has been developed to perform an X-ray imaging regardless of places.

Due to an X-ray source being mounted to a mobile body, and a portable X-ray detector, the mobile X-ray imaging apparatus may come to the patient having movement difficulties so as to perform X-ray imaging.

SUMMARY

To address the above-discussed deficiencies, it is a primary object to provide an X-ray apparatus capable of releasing a locked rotation of a wheel using a power supplied from an auxiliary battery of an X-ray detector when a body is discharged, and a control method thereof.

Additional aspects of the present disclosure will be set forth in part in the description which follows and, in part, will be obvious from the description, or may be learned by practice of the disclosure.

In accordance with one aspect of the present disclosure, a mobile X-ray apparatus includes a body including a body battery, a detector accommodator provided at an outside of the body, and a wheel provided at a lower side of the body, an X-ray source coupled to the body and configured to emit X-rays to an object, a detector battery connector provided on the body and connectable to a detector battery that is mountable on an X-ray detector for detecting X-rays emitted by the X-ray source, a power supply circuit connected to the detector battery connector to form a first path in which a power is supplied from the body battery to the detector battery and a second path in which a power is supplied from the detector battery to the body and a controller configured to control the power supply circuit to selectively form the first path and the second path.

The controller may control the power supply circuit to form the first path in which a power is supplied from the body battery to the detector battery connector when the body battery is capable of supplying a power.

The controller may control the power supply circuit to form the second path in which a power is supplied from the detector battery to the body when the body battery is incapable of supplying a power.

The power supply circuit may further include a detector battery recognizer configured to determine whether the detector battery is connected to the detector battery connector, and the controller may control the power supply circuit to block the first path when the detector battery is not connected to the detector battery connector.

The detector battery connector may be positioned at the detector accommodator provided on a surface of the outside of the body, and the detector battery connector may be connectable to the detector battery mounted on the X-ray detector when the X-ray detector is accommodated in the detector accommodator.

The detector battery connector may be provided on a detector battery coupler that is provided on a lower end of a handle of the body to guide the detector battery such that the detector battery is connected to the detector battery connector.

The body may further include a wheel driver configured to provide the wheel with a torque using the power supplied from the body battery and a brake configured to lock a rotation of the wheel, the controller may control the brake such that the wheel is rotatable by the power supplied from the detector battery when the rotation of the wheel is prevented.

The power supply circuit may include a first converter configured to reduce a voltage of the power supplied from the body battery to the brake and a second converter configured to reduce a voltage of the power supplied from the body battery to the detector battery.

The power supply circuit may further include a third converter configured to increase a voltage of the power supplied from the detector battery to the brake.

The power supply circuit may further include a first switch configured to form a path in which a power is supplied to the brake from one of the body battery and the detector battery.

The power supply circuit may further include a second switch configured to transmit or block a power supplied to the brake.

The power supply circuit may further include a third switch configured to transmit the power, a voltage of which is increased by the third converter, to the brake.

The power supply circuit may further include a fourth switch configured to transmit the power, a voltage of which is reduced by the first converter, to the brake.

In accordance with another aspect of the present disclosure, a mobile X-ray apparatus includes a body including a body battery, a detector accommodator provided at an outside of the body, and a wheel provided at a lower side of the body, an X-ray source coupled to the body and configured to emit X-rays to an object, a detector battery connector provided on the body and connectable to a detector battery that is mountable on an X-ray detector for detecting X-rays emitted by the X-ray source, a power supply circuit connected to the detector battery connector to form a first path in which a power is supplied from the body battery to the detector battery and a second path in which a power is supplied from the detector battery to the body, a controller configured to control the power supply circuit to selectively form the first path and the second path and an auxiliary input configured to receive a rotation unlock command of the wheel. The controller may control the power supply circuit to form the second path along which a power is supplied from the detector battery to the body when the rotation unlock command is received through the auxiliary input.

The body may further include a wheel driver configured to provide the wheel with a torque using the power supplied from the body battery and a brake configured to lock a rotation of the wheel. The controller may control the brake such that the wheel is rotatable by the power supplied from the detector battery when the rotation unlock command is received.

The auxiliary input may be provided on a handle provided on the body.

In accordance with another aspect of the present disclosure, A method of controlling a mobile X-ray apparatus includes locking a rotation of a wheel provided on a body when a body battery provided on the body of the mobile X-ray apparatus is incapable of supplying a power, and receiving a power control command of the mobile X-ray apparatus and in response to receiving the power control command, forming a second path in which a power is supplied to the body from a detector battery that is connectable to a detector battery connector of the body.

The method may further include forming a first path in which a power is supplied from the body battery to the detector battery when the body battery is capable of supplying a power.

The receiving of the power control command may include receiving a rotation unlock command of the wheel through an auxiliary input that is provided on the body, and the forming of the second path may include, in response to receiving the rotation unlock command of the wheel, forming a power supply path in which a power of the detector battery is supplied to a brake provided on the body such that the wheel is rotatable.

The method may further include supplying a power of the detector battery to the brake.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1A through 13, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged X-ray apparatus. The present disclosure will now be described more fully with reference to the accompanying drawings, in which exemplary embodiments of the disclosure are shown.

Figure 1A:
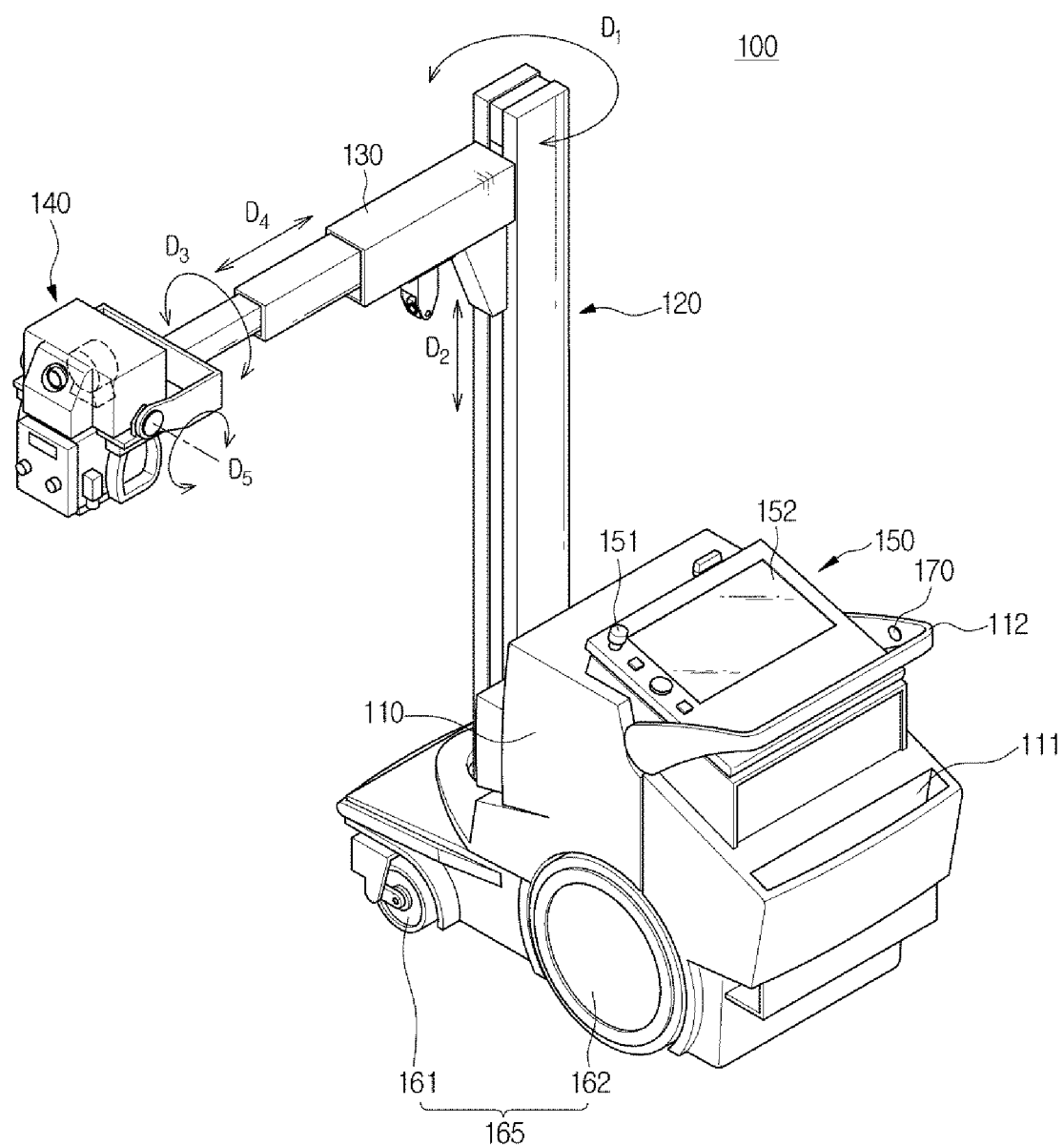
FIGS. 1A and 1B illustrate a configuration of an X-ray apparatus in accordance with one embodiment.
Figure 1B:
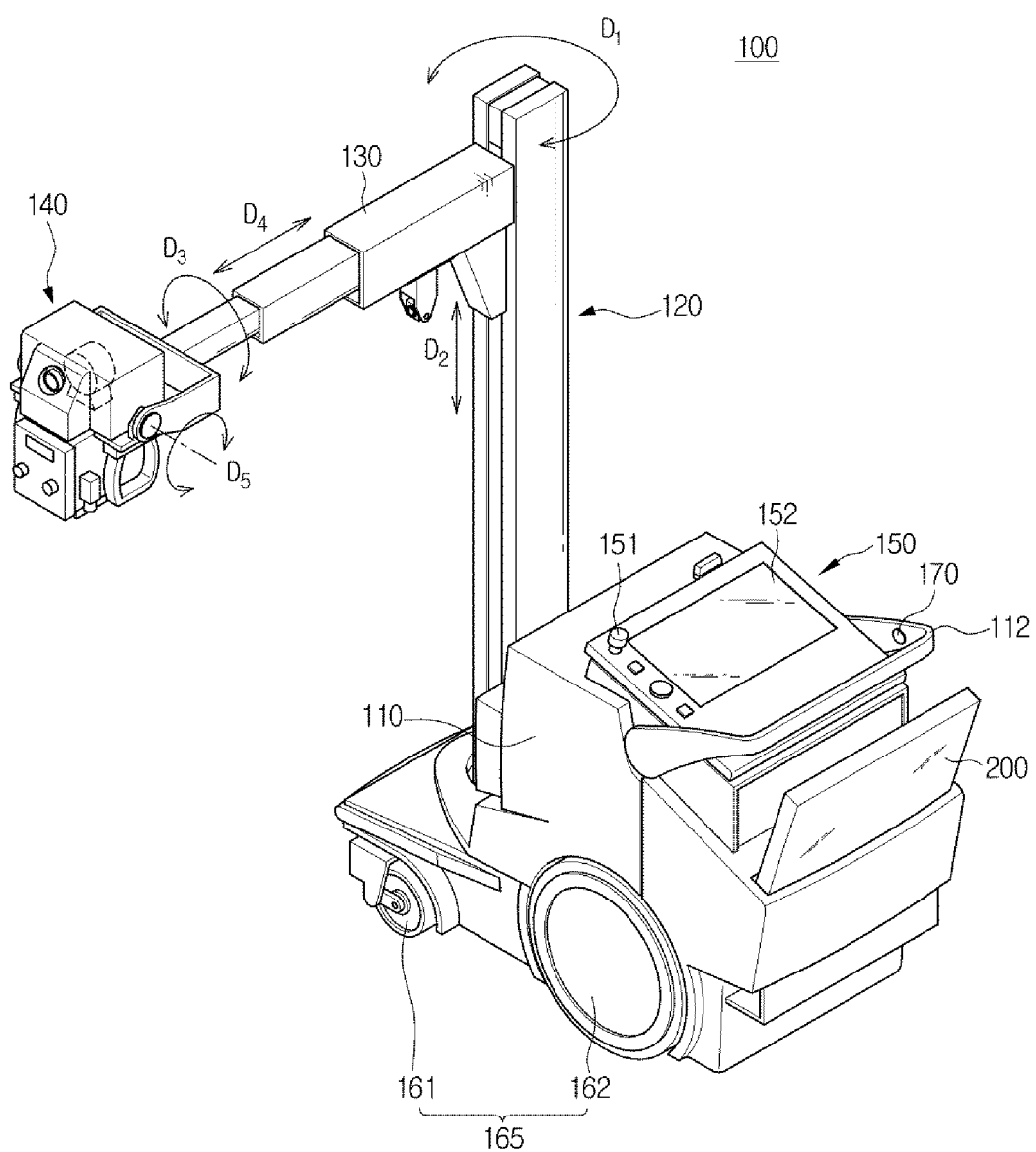
Figure 2A:
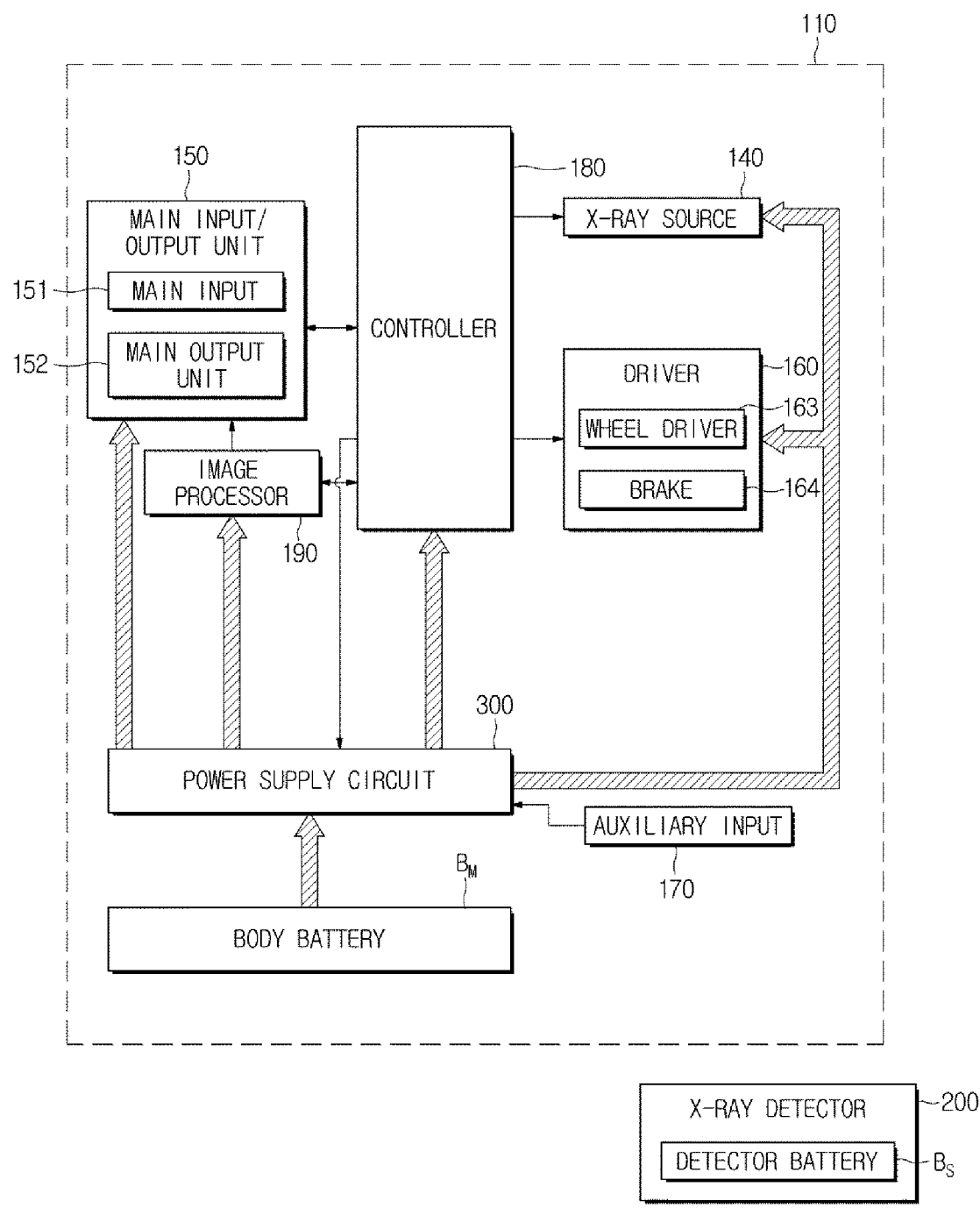
FIGS. 2A and 2B illustrate a control flow and a power flow of the X-ray apparatus in accordance with one embodiment.
Figure 2B:
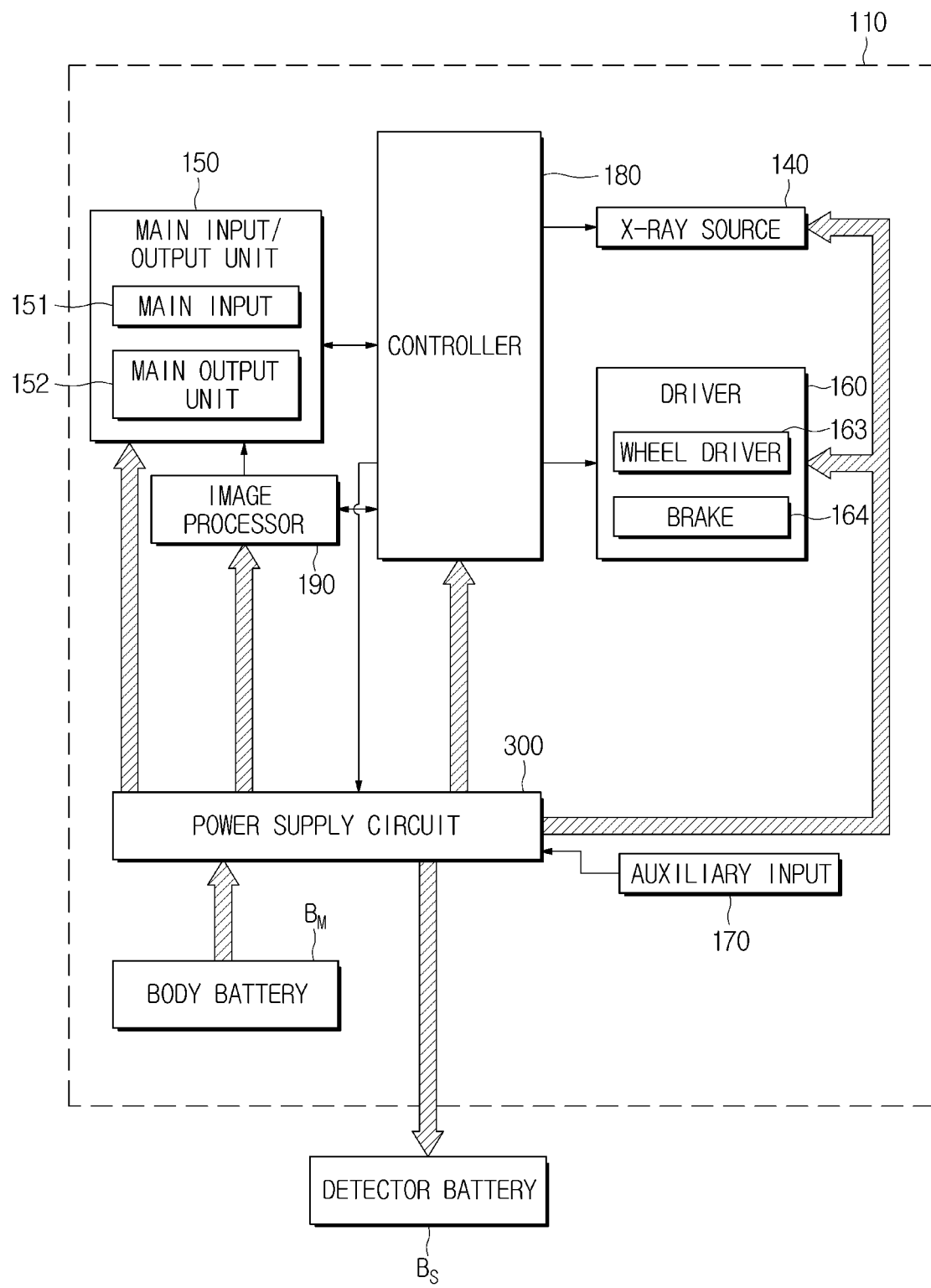

FIGS. 1A and 1B illustrate a configuration of an X-ray apparatus in accordance with one embodiment. FIGS. 2A and 2B illustrate a control flow and a power flow of the X-ray apparatus in accordance with one embodiment. In FIGS. 2A and 2B, a general arrow illustrates a control flow and a thick arrow illustrates a power flow.

Referring to FIGS. 1A and 2A, according to one embodiment, an X-ray apparatus 100 may include a body 110; a wheel 165 provided in a lower side of the body 110 to allow the X-ray apparatus 100 to be movable; and an X-ray detector 200 configured to be placed in the body 110. In addition, an image processor 190 is configured to generate an X-ray image based on X-rays detected by the X-ray detector 200; a driver 160 configured to supply an external force to the wheel 165 for the movement; a controller 180 configured to control a component of the X-ray apparatus 100; a body battery (BM) configured to provide a power which is then supplied to the each component of the X-ray apparatus 100; and a power supply circuit 300 configured to transmit the power supplied from the body battery (BM) to each component of the body 110 may be provided in the inside of the body 110. As illustrated in FIG. 1A, an X-ray source 140 configured to emit X-rays to an object; a main input/output unit 150 configured to perform an input and output by a user; and a detector accommodation unit 111 provided with a space in which the X-ray detector is accommodated may be provided in the exterior of the body 110.

The main input/output unit 150 may be provided on one side of the body 110. The main input/output unit 150 may perform an input and output by the user, and for this, the main input/output unit 150 may include a main input 151 and a main output unit 152.

The main output unit 152 may output an X-ray image in a visual manner. In this time, the X-ray image output by the main output unit 152 may include an X-ray image generated based on the X-rays detected by the X-ray detector 200 and an X-ray image that is pre-stored in an external storage medium or a server.

At the same time, the main output unit 152 may visually output a control screen to receive an input of a control command related to an X-ray image that is outputting. For example, the main output unit 152 may output a control screen to input a command, wherein the command may include a command to magnify and de-magnify an X-ray image that is outputting, a selection command to select at least one of a plurality of X-ray images, a marking command to mark a certain position or area in an X-ray image, and a command to modify an X-ray image.

The main output unit 152 may visually output information related to the X-ray apparatus 100 together with the X-ray image or visually output the information separated from the X-ray image. For example, the main output unit 152 may visually output power information of the X-ray apparatus 100, location information of the X-ray source 140 and rotation information of the wheel 165.

For this, the main output unit 152 may be implemented by at least one of well-known display panels.

The main input 151 may receive an input of a control command related to the X-ray apparatus 100. Particularly, the main input 151 may receive an input of a control command related to an X-ray image output via the main output unit 152. The main input 151 may receive an input of a command, wherein the command may include a command to magnify and de-magnify an X-ray image that is outputting from the main output unit 152, a selection command to select at least one of a plurality of X-ray images, a marking command to mark a certain position or area in an X-ray image, and a command to modify an X-ray image.

In addition, the main input 151 may receive an input of a control command related to an entire operation of the X-ray apparatus 100. For example, the main input 151 may receive an input of a command, wherein the command may include a power control command of the X-ray apparatus 100, a moving command of the X-ray source 140, a rotation command of the wheel 165 and a rotation lock command of the wheel 165. For this, the main input 151 may be implemented by a key board, a mouse, a track ball, a jog shuttle, and a touch pad.

When the main input 151 is implemented by a touch pad and disposed on a front surface of the main output unit 152, the main input 151 together with the main output unit 152 may be implemented by a single touch screen.

The X-ray source 140 may emit X-rays to an object. For this, the X-ray source 140 may include an X-ray tube and a collimator.

In order to emit X-rays to a position that is a target for acquiring an X-ray image, the X-ray source 140 may be provided to be free to move with respect to the body 110. For this, the body 110 may include a support 120 provided to be perpendicular to the ground, and the X-ray source 140 may be coupled to the support 120 via an arm 130.

The support 120 may be provided to be rotatable in a D1 direction. In addition, a rail may be formed on the support 120 in a D2 direction so that the arm 130 is vertically movable. An end of the arm 130 may be coupled to the support 120 to be movable along the rail of the support 120, and the other end of the arm 130 may be coupled to the X-ray source 140. As a result, the X-ray source 140 coupled to the arm 130 may be movable in a direction perpendicular to the ground in which the rail of the support 120 is formed, that is, in the D2 direction. In addition, the X-ray source 140 may be rotatable with respect to the support according to a rotation of the support in the D1 direction. In addition, the support 120 may be formed to have two steps, which are interlocked to each other, so that an upper end to which the arm 130 is coupled is extended in a direction perpendicular to a lower end fixed to the body 110.

The arm 130 may include a rotation joint configured to be rotatable in a plurality of D3 directions. In addition, a length of the arm 130 may be adjustable in the vertical direction of the support 120, that is, a straight direction of D4. Therefore, according to an extension or contraction of the length of the arm 130 or the rotation of the arm 130, the X-ray source 140 coupled to the other end of the arm 130 may be movable in the D3 and D4 direction. In addition, the X-ray source 140 may be pivotable in D5 direction.

The X-ray apparatus 100 may include an additional motor configured to provide a force to move the X-ray source 140 in the D1 to D5 directions. Alternatively, the X-ray apparatus 100 may be manually movable by a user. The detector accommodation unit 111 provided in the exterior of the body 110 may include a space in which the X-ray detector 200 is accommodated. FIG. 1A illustrates that the X-ray detector 200 is not placed in the detector accommodation unit 111, and FIG. 1B illustrates that the X-ray detector 200 is placed in the detector accommodation unit 111. The user may place the X-ray detector 200 in the detector accommodation unit 111 as needed. Accordingly, when moving the body 110, the X-ray detector 200 may be moved together with the body 110 and the X-ray detector 200 may be easily stored.

The X-ray detector 200 may detect X-rays and generate an electric signal corresponding to the X-rays. For this, the X-ray detector 200 may employ at least one method in well-known methods for detecting X-rays.

The X-ray detector 200 may include a detector battery (BS) configured to be detachable so that the X-ray detector 200 is independently operable while being separated from the body 110. A description thereof will be described later.

The electric signal generated by the X-ray detector 200 may be transmitted to the image processor 190 inside of the body 110. The image processor 190 may process the generated electric signal based on the detected X-rays so as to generate an X-ray image of an object. The generated X-ray image may be visually output by the above mentioned main output unit 152.

The X-ray image generated by the image processor 190 may include anatomical information of the object and thus the user may check the anatomical structure of the inside of the object based on the X-ray image output by the main output unit 152.

The wheel 165 may be provided to be rotatable in a lower side of the body 110. FIGS. 1A and 1B illustrate that two front wheels provided adjacent to the support 120 in the lower portion of the body 110 and two rear wheels provided far from the support 120 in the lower portion of the body 110 are provided, but the number of the wheel 165 is not limited thereto.

A handle 112 may be provided on the exterior of the body 110 so that the user easily controls a moving direction of the body 110 when moving the body 110. The user may change or maintain the moving direction of the body 110 or control a moving speed by holding the handle 112.

The driver 160 may include a wheel driver 163 providing a torque to the wheel 165 and a brake 164 stopping a rotation of the wheel 165.

The wheel driver 163 may be implemented by a driving motor, and the wheel driver 163 may be connected to an entire of the wheel 165 or some of the wheel 165. For example, the wheel driver 163 may be connected to only the rear wheel 162 to provide the torque and then the front wheel 161 may be rotated according to the rotation of the rear wheel 162.

The brake 164 may provide a frictional force to the rotating wheel 165 to stop the rotation of the wheel 165. For this, the brake 164 may be implemented in an electric manner, e.g. a solenoid. When the power is not applied to the brake 164, the brake 164 may stop the rotation of the wheel 165 by providing the frictional force to a drive shaft of the wheel driver 163. In contrast, when the power is applied, the brake 164 may be apart from the drive shaft of the wheel driver 163 so that the wheel 165 may be converted into a state in which the wheel 165 is free to be rotatable.

The controller 180 may control each component of the body 110. For example, when performing an X-ray imaging, the controller 180 may control the main output unit 152 so that the main output unit 152 outputs a screen for the control of the X-ray imaging, and control the main input 151 so that the main input 151 receives an input of a command for the X-ray imaging. When the command for the X-ray imaging is input, the controller 180 may control the X-ray source 140 so that X-rays are emitted to the object.

As another example, when the user wants to move the X-ray apparatus 100 to a desired location, the controller 180 may control the main output unit 152 so that the main output unit 152 outputs a screen to control the movement of the body 110 and control the main input 151 so that the main input 151 receives a movement control command of the body 110. According to the input control command, the controller 180 may move the X-ray apparatus 100 by controlling the wheel driver 163 and/or the brake 164.

The body battery (BM) may be provided inside of the body 110 to provide the power. According to the disclosed embodiment, the movement of the location the X-ray apparatus 100 may be free by the wheel 165, and thus the X-ray apparatus 100 may be provided with an independent body battery (BM) other than commercial electricity.

The power supply circuit 300 may be connected to the body battery (BM) to form a path, to which a power provided from the body battery (BM) is supplied, according to the control of the controller 180. Referring to FIG. 2A, the power supply circuit 300 may supply the power provided from the body battery (BM) to the main input/output unit 150, the controller 180, the X-ray source 140 and the driver 160.

As mentioned above, the X-ray detector 200 may be provided with the detector battery (BS) configured to be detachable so that the X-ray detector 200 is independently operable when separated from the body 110. In this time, the power supply circuit 300 may supply the power supplied from the body battery (BM) to the detector battery (BS) to charge the detector battery (BS) of the X-ray detector 200. FIG. 2B illustrates that the detector battery (BS) is charged by the body battery (BM).

When the X-ray apparatus 100 does not perform an X-ray imaging, the X-ray apparatus 100 may charge the detector battery (BS) using the body battery (BM) so that a malfunction or unfunction caused by the discharge of the X-ray detector 200 may be prevented in advance and the mobility of the X-ray detector 200 may be improved.

When the body battery (BM) is completely discharged or the output of the power is blocked due to detecting a danger in the body battery (BM) by Battery Management System (BMS), that is, the body battery (BM) is in a state incapable of supplying the power, the brake 164 may lock the rotation of the wheel 165. When the X-ray apparatus 100 is not moved in a desired direction since the power is not supplied to the wheel driver 163, the brake 164 may lock the rotation of the wheel 165 to fix the X-ray apparatus 100 to a current position so that the safety of the X-ray apparatus 100 and a user are secured.

In this case, it may be required for the user to charge or replace the body battery (BM) to restart the movement of the X-ray apparatus 100. However, it may require a considerable time to charge the body battery (BM), and it may be not easy for the user to replace the body battery (BM) since the body battery (BM) is placed inside of the body 110.

According to the disclosed embodiment, when the rotation of the wheel 165 is locked, the X-ray apparatus 100 may control the brake 164 so that the lock of the wheel 165 is released by the power supplied from the detector battery (BS).

Figure 3:
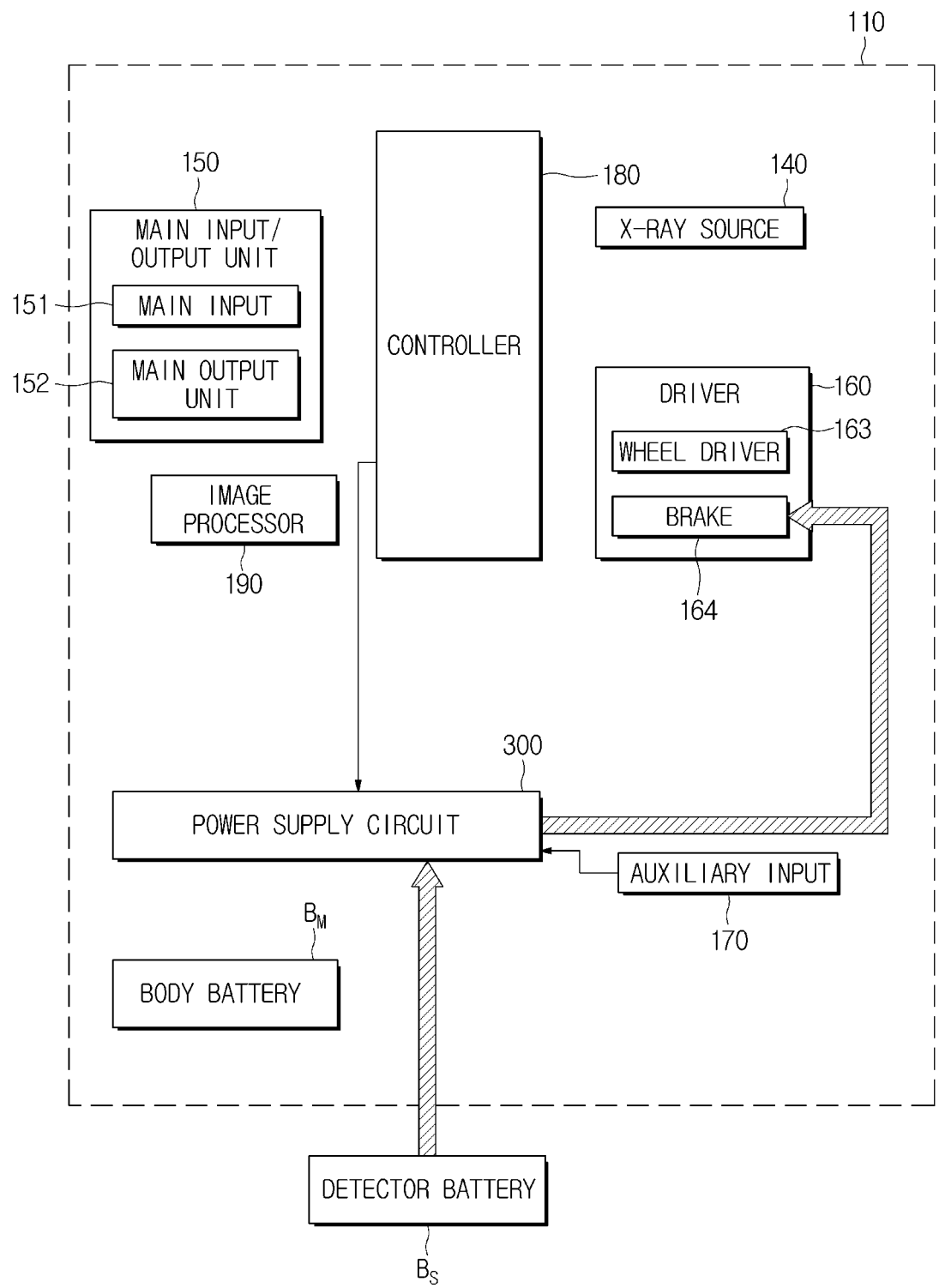
FIG. 3 illustrates a power flow when the body battery of the X-ray apparatus is in a state incapable of supplying the power in accordance with one embodiment.

FIG. 3 illustrates a power flow when the body battery of the X-ray apparatus is in a state incapable of supplying the power in accordance with one embodiment.

When the body battery (BM) is discharged or the output of the power of the body battery (BM) is blocked, the controller 180 may control the power supply circuit 300 so that the power supplied via the detector battery (BS) is supplied to the brake 164. The brake 164 receiving the power may release the locked rotation of the wheel 165 and when the locked rotation of the wheel 165 is released, the user may rotate the wheel 165 by applying an external force so as to move the X-ray apparatus 100.

In this time, only when a rotation unlock command of the wheel 165 is input, the controller 180 may control the brake 164 so that the locked rotation of the wheel 165 is released by the power supplied from the detector battery (BS). For this, according to the disclosed embodiment, the X-ray apparatus 100 may further include an auxiliary input 170 configured to receive the rotation unlock command of the wheel 165.

When the rotation of the wheel 165 is locked due to an abnormal operation of the body battery (BM), the auxiliary input 170 may be provided on an external location of the body 110 so that the user easily unlocks the wheel 165. The above mentioned FIGS. 1A and 1B illustrate a case in which the auxiliary input 170 is formed in the handle 112, but the position of the auxiliary input 170 is not limited thereto.

Through this, in a state in which the body battery (BM) is incapable of supplying the power, it may be possible to prevent that the rotation of the wheel 165 is unlocked regardless of the user's intention.

Hereinafter an operation of the power supply circuit 300 in a state in which the body battery (BM) is incapable of supplying the power will be described in details.

Figure 4:
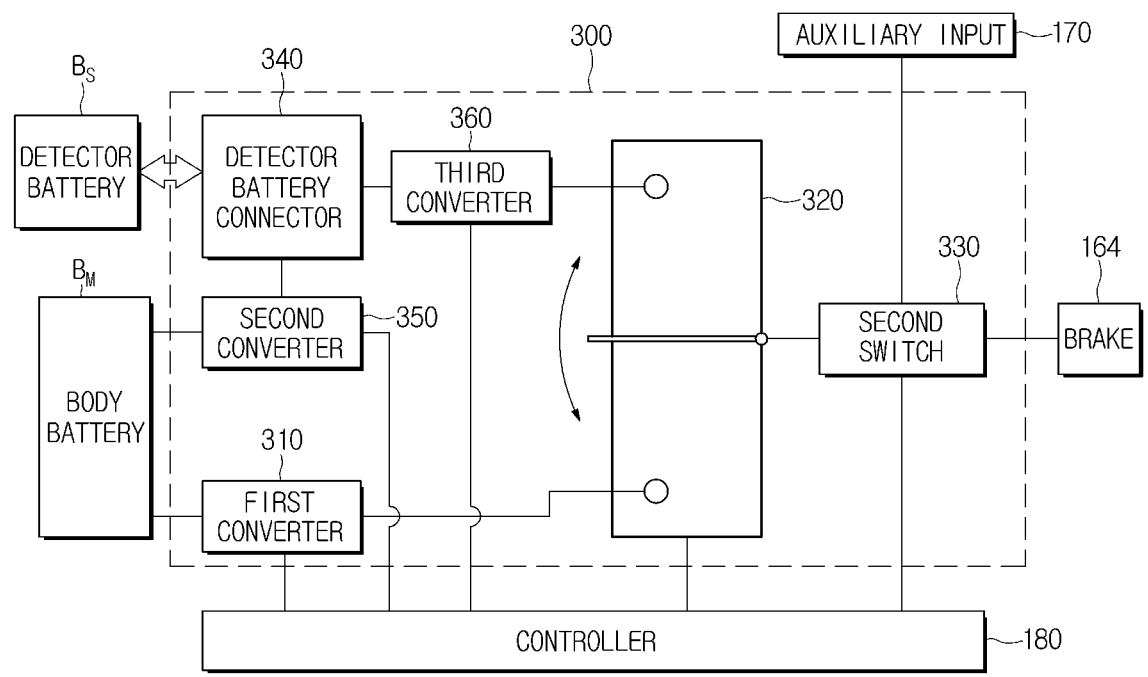
FIG. 4 illustrates a configuration of the power supply circuit in accordance with one embodiment of the present disclosure.
Figure 5:
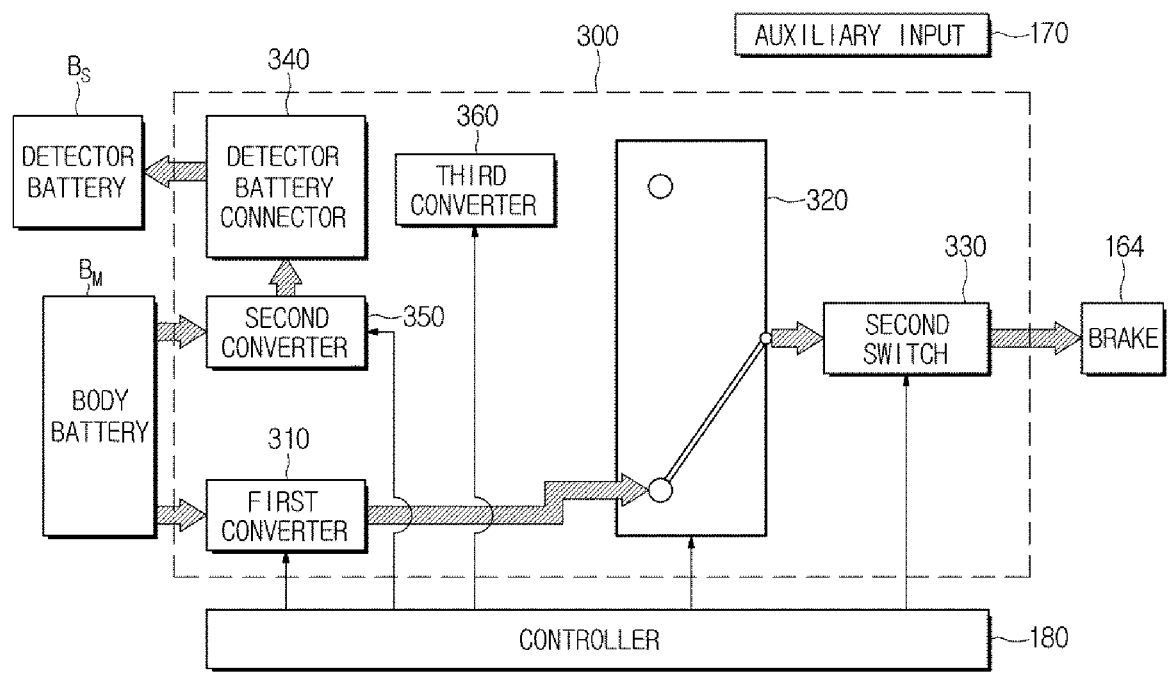
FIG. 5 illustrates a first power supply path of the power supply circuit in accordance with one embodiment of the present disclosure.
Figure 6:
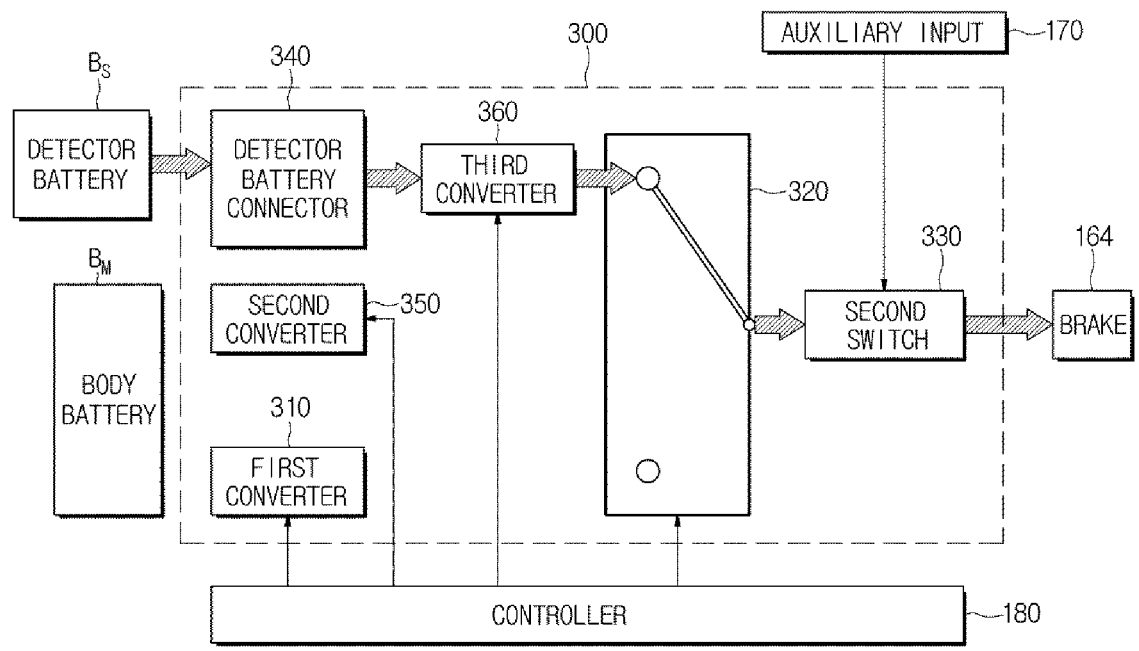
FIG. 6 illustrates a second power supply path of the power supply circuit in accordance with one embodiment of the present disclosure.

FIG. 4 illustrates a configuration of the power supply circuit in accordance with one embodiment of the present disclosure, FIG. 5 illustrates a first power supply path of the power supply circuit in accordance with one embodiment of the present disclosure, and FIG. 6 illustrates a second power supply path of the power supply circuit in accordance with one embodiment of the present disclosure. In FIGS. 5 and 6, a general arrow illustrates a control flow and a thick arrow illustrates a power flow.

Referring to FIG. 4, according to one embodiment, the power supply circuit 300 may include a first converter 310 converting a voltage of the power supplied from the body battery (BM) to the brake 164; a second converter 350 converting a voltage of the power supplied from the body battery (BM) to the detector battery (BS); a third converter 360 converting a voltage of the power supplied from the detector battery (BS) to the brake 164; a first switch 320 forming a path in which the power is supplied from at least one of the body battery (BM) and the detector battery (BS); and a second switch 330 transmitting or blocking the power to the brake 164.

In this time, the first switch 320 may be implemented by a relay switch and the second switch 330 may be implemented by a field effect transistor (FET) to allow ON/OFF control.

Referring to FIG. 5, when the body battery (BM) is normally operated, i.e., the body battery (BM) is in a state capable of supplying the power, the controller 180 may control the first switch 320 and the second switch 330 to form the first power supply path. As a result, the first power supply path in which the body battery (BM)—the first converter 310—the first switch 320—the second switch 330—the brake 164 are connected may be formed.

A process of supplying the power to the brake 164 along the first power supply path may be formed as follows.

Since the power supplied from the body battery (BM) is greater than a power for the operation of the brake 164, the first converter 310 may reduce the voltage of the power supplied from the body battery (BM). For example, when the body battery (BM) supplies a power of 360V, the first converter 310 may convert 360V into 24V.

When the body battery (BM) is normally operated, the first switch 320 may connect the first converter 310 to the second switch 330, and the second switch 330 may be maintained to be turned on. Therefore, the power that is converted via the first converter 310 may be transmitted to the brake 164 through the first switch 320 and the second switch 330.

When the body battery (BM) is normally operated, the power supply circuit 300 may form a charging path of the detector battery (BS). As a result, the charging path in which the body battery (BM)—the second converter 350—a detector battery connector 340—the detector battery (BS) are connected may be formed.

Since the power supplied from the body battery (BM) is greater than a power for the charge of the detector battery (BS), the second converter 350 may reduce the voltage of the power supplied from the body battery (BM). For example, when the body battery (BM) supplies a power of 360V, the second converter 350 may convert 360V into 19V.

The detector battery connector 340 may connect the detector battery (BS) to the power supply circuit 300. As a result, the power that is converted by the second converter 350 may be transmitted to the detector battery (BS) through the detector battery connector 340 and finally the detector battery (BS) may be charged.

In this time, the controller 180 may block the operation of the third converter 360. Since the above mentioned charging path is connected to the third converter 360, the charging power may be delivered to the brake 164 and thus there may be a concern that a malfunction of the brake 164 is generated. Therefore, the operation of the third converter 360 may be stopped by the control of the controller 180 when the output of the body battery (BM) is present.

Referring to FIG. 6, when the body battery (BM) is abnormally operated, i.e., the body battery (BM) is in a state incapable of supplying the power, the controller 180 and the auxiliary input 170 may control the first switch 320 and the second switch 330 to form a second power supply path. As a result, the second power supply path in which the detector battery (BS)—the third converter 360—the first switch 320—the second switch 330—the brake 164 are connected may be formed.

A process of supplying the power to the brake 164 along the second power supply path may be formed as follows.

Since the power supplied from the detector battery (BS) is less than a power for the operation of the brake 164, the third converter 360 may increase the voltage of the power supplied from the detector battery (BS). For example, when the detector battery (BS) supplies a power of 12V, the third converter 360 may convert 12V into 24V.

When the body battery (BM) is abnormally operated, the first switch 320 may connect the third converter 360 to the second switch 330. In addition, when the auxiliary input 170 receives the rotation unlock command of the wheel 165, the second switch 330 may be converted into a turned-on state, and thus the power that is converted via the third converter 360 may be delivered to the brake 164 through the first switch 320 and the second switch 330.

Hereinbefore a case in which the power supply circuit 300 includes the first switch 320 implemented by the relay switch and the second switch 330 implemented by the FET is illustrated as an example. Hereinafter a power supply circuit in accordance with another embodiment will be described with reference to FIG. 7.

Figure 7:
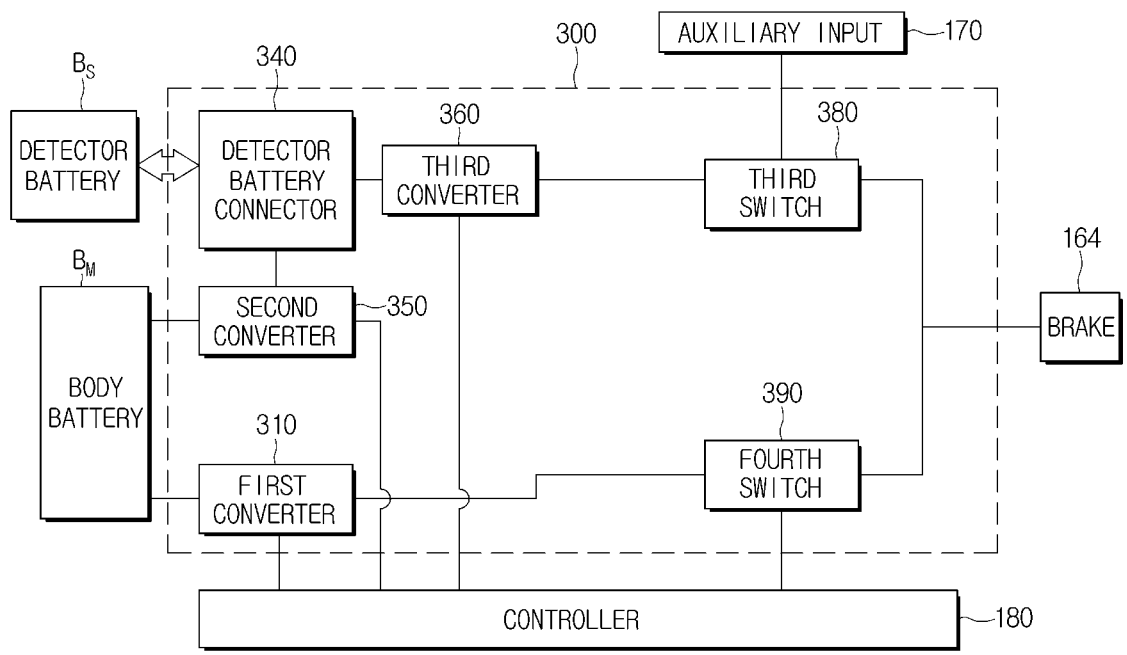
FIG. 7 illustrates a configuration of a power supply circuit in accordance with another embodiment of the present disclosure.

FIG. 7 illustrates a configuration of a power supply circuit in accordance with another embodiment of the present disclosure.

Referring to FIG. 7, according to another embodiment, a power supply circuit may include a first converter 310 converting a voltage of the power supplied from the body battery (BM) to a brake 164; a second converter 350 converting a voltage of the power supplied from the body battery (BM) to the detector battery (BS); a third converter 360 converting a voltage of the power supplied from the detector battery (BS) to the brake 164; a third switch 380 transmitting the power converted by the third converter to the brake; and a fourth switch 390 transmitting the power converted by the first converter to the brake.

The power supply circuit according to the embodiment of FIG. 7 may be different from the power supply circuit of FIG. 4 in that the power supply circuit of FIG. 7 includes the third switch and the fourth switch, and thus a description of the same part will be omitted.

The third switch and the fourth switch may be implemented by the FET to allow ON/OFF control. In addition, the third switch may be turned on or off depending on an input via the auxiliary input 170 while the fourth switch is turned on or off depending on the control of the controller 180.

When the body battery (BM) is normally operated, i.e., the body battery (BM) is in a state capable of supplying the power, the controller 180 may control the fourth switch 390 so that the fourth switch 390 forms a first power supply path. As a result, the first power supply path in which the body battery (BM)—the first converter 310—the fourth switch 390—the brake 164 are connected may be formed.

Meanwhile, when the body battery (BM) is abnormally operated, i.e., the body battery (BM) is in a state incapable of supplying the power, the auxiliary input 170 may control the third switch 380 so that the third switch 380 forms a second power supply path. As a result, the second power supply path in which the detector battery (BS)—the third converter 360—the third switch 380—the brake 164 are connected may be formed.

As mentioned above, in a state in which a charging path is formed, when the detector battery connector 340—the third converter 360—the first switch 320—the second switch 330 or the detector battery connector 340—the third converter 360—the third switch 380 are connected to each other, the charging power that is converted by the second converter 350 may be delivered to the brake 164. As a result, it may be possible to generate a malfunction of the brake 164 caused by the charging power.

Therefore, the controller 180 may determine whether the second converter 350 is operated according to whether the detector battery (BS) is connected to the detector battery connector 340. The power supply circuit 300 may further include a detector battery recognizer 370 to determine whether the detector battery (BS) is connected to the detector battery connector 340.

Figure 8:
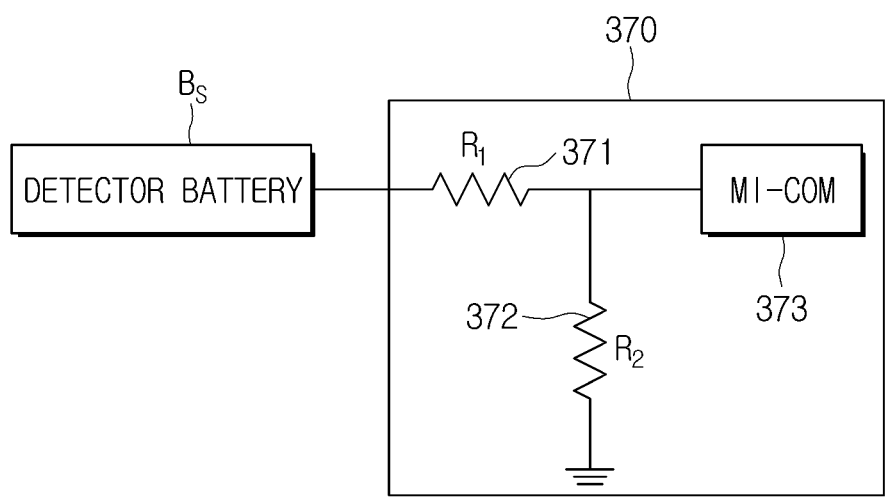
FIG. 8 illustrates a detector battery recognizer in accordance with one embodiment.
Figure 9:
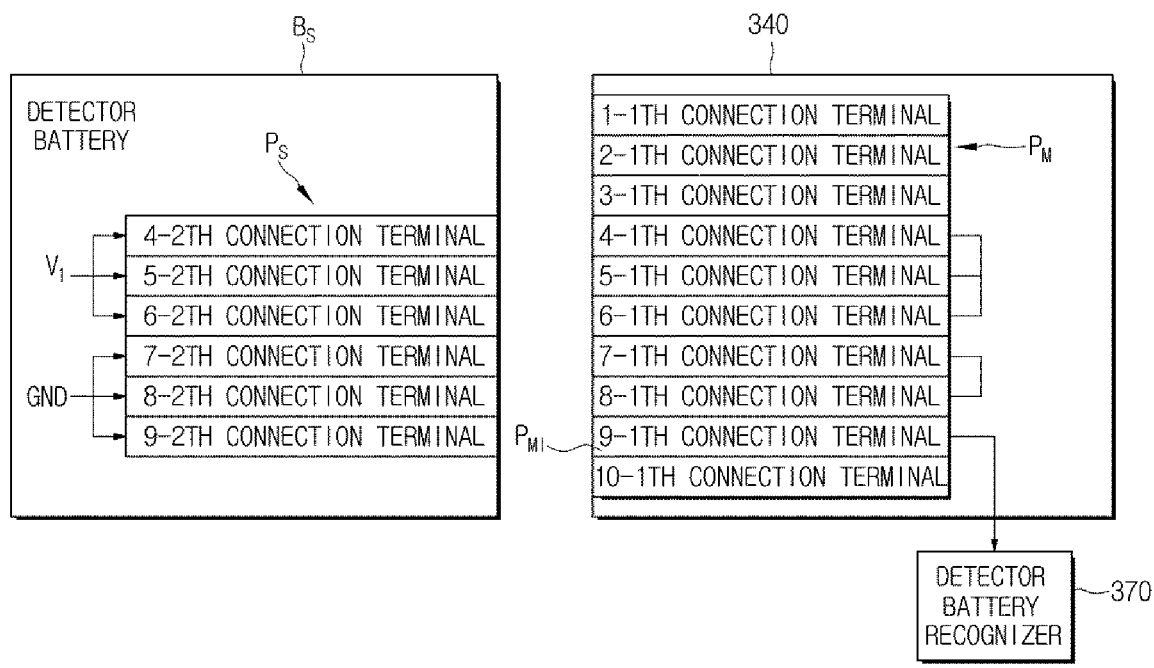
FIG. 9 illustrates a detector battery recognizer in accordance with another embodiment.

FIG. 8 illustrates a detector battery recognizer in accordance with one embodiment, and FIG. 9 illustrates a detector battery recognizer in accordance with another embodiment. For convenience of description, the detector battery connector 340 may be omitted in FIG. 8.

The detector battery recognizer 370 according to one embodiment may form a voltage dividing circuit inside thereof. In addition, the detector battery recognizer 370 may include a mi-com 373 configured to confirm a voltage of a predetermined node in the voltage dividing circuit. When the voltage of the predetermined node is equal to or more than a threshold, the detector battery recognizer 370 may determine that the detector battery (BS) is connected to the detector battery connector 340.

Referring to FIG. 8, the detector battery recognizer 370 may form the voltage dividing circuit including a first resistance (R1) 371 and a second resistance (R2) 372. In addition, the first resistance (R1) 371 may be connected to a node, which may be connected when the detector battery (BS) is connected, and the mi-com 373 may confirm a voltage of a branch node (A) between the first resistance (R1) 371 and the second resistance (R2) 372. When R1 and R2 are 10 kΩ and a threshold is 4.5V, the detector battery recognizer 370 may confirm whether the detector battery (BS) outputting a voltage of from 9 to 12.6V is connected.

The detector battery recognizer 370 according to another embodiment may be connected to an identification terminal (PMI) among a connection terminal (PM) of the detector battery connector 340 connected to a connection terminal (PS) of the detector battery (BS). The detector battery recognizer 370 may determine whether the detector battery (BS) is connected, by confirming a voltage of the identification terminal (PMI).

Referring to FIG. 9, the detector battery connector 340 may include the detector battery connector side-connection terminal (PM) including from 1-1th connection terminal to 10-1th connection terminal. Among these, 4-1th connection terminal to 9-1th connection terminal may be connected to 4-2th connection terminal to 9-2th connection terminal in the detector battery side-connection terminal (PS), and 9-1th connection terminal as the identification terminal (PMI) may be connected to the detector battery recognizer 370.

In this time, in the detector battery side-connection terminal (PS), a voltage of V1 may be applied to from 4-2th connection terminal to 6-2th connection terminal and from 7-2th connection terminal to 9-2th connection terminal may be grounded. In addition, in the detector battery connector side-connection terminal (PM), from 4-1th connection terminal to 6-1th connection terminal may be short, and from 7-1th connection terminal to 8-1th connection terminal may be short.

When the detector battery (BS) is connected to the detector battery connector 340, 9-2th connection terminal that is grounded may be connected to 9-1th connection terminal (PMI) and thus 9-1th connection terminal (PMI) may represent a ground potential.

Meanwhile, when the detector battery (BS) is not connected to the detector battery connector 340, 7-1th connection terminal, 8-1 connection terminal, and 9-1 connection terminal (PMI) in the open state may represent the open potential.

When a potential of the identification terminal (PMI) is a ground potential, the detector battery recognizer 370 may determine that the detector battery (BS) is connected, and when a potential of the identification terminal (PMI) is an open potential, the detector battery recognizer 370 may determine that the detector battery (BS) is not connected.

According to the above mentioned method, when the detector battery recognizer 370 determines whether the detector battery (BS) is connected, a result of the determination may be delivered to the controller 180, and the controller 180 may control an operation of the second converter 350 according to the result of the determination. Alternatively, the detector battery recognizer 370 may directly deliver a result of the determination to the second converter 350 and thus the second converter 350 may determine whether to operate, by itself.

The detector battery (BS) may be connected to the body 110 in a variety of methods. Hereinafter a connection method of the detector battery (BS) to the body 110 will be described with reference to FIGS. 10 and 11A and 11B.

Figure 10:
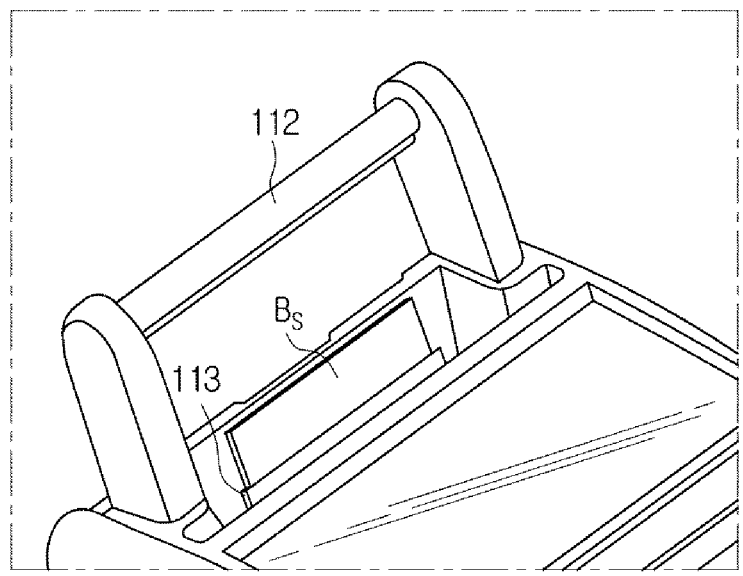
FIG. 10 illustrates a detector battery coupling unit in accordance with one embodiment.
Figure 11A:
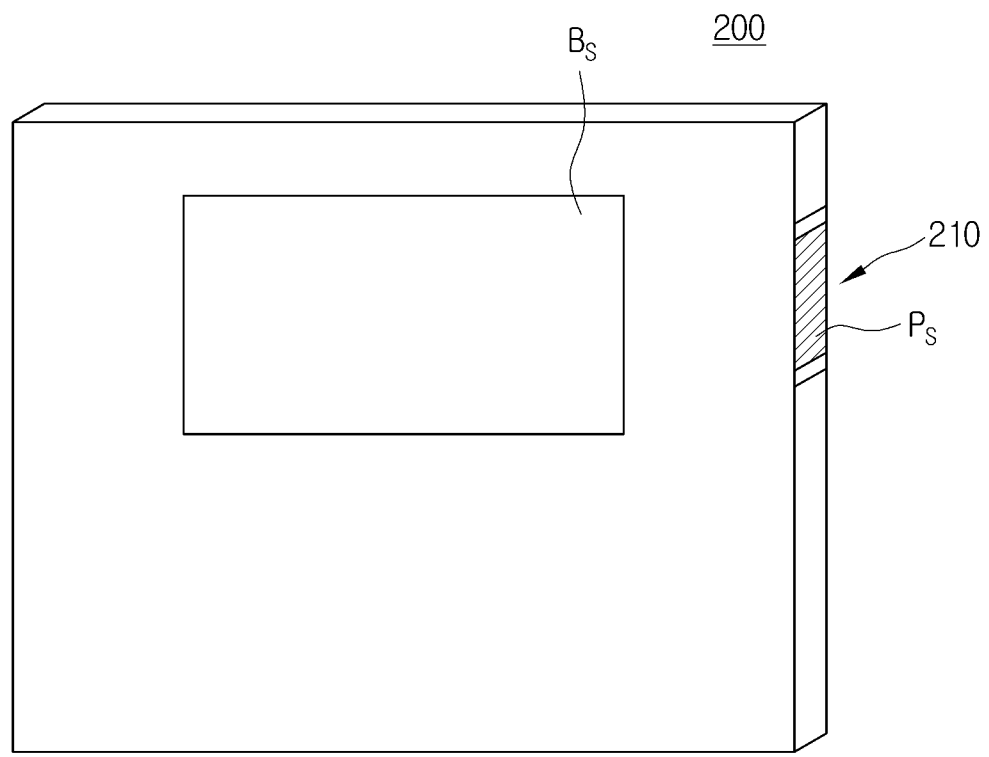
FIGS. 11A and 11B illustrates a position of a detector battery side connection terminal in accordance with a variety of embodiments.
Figure 11B:
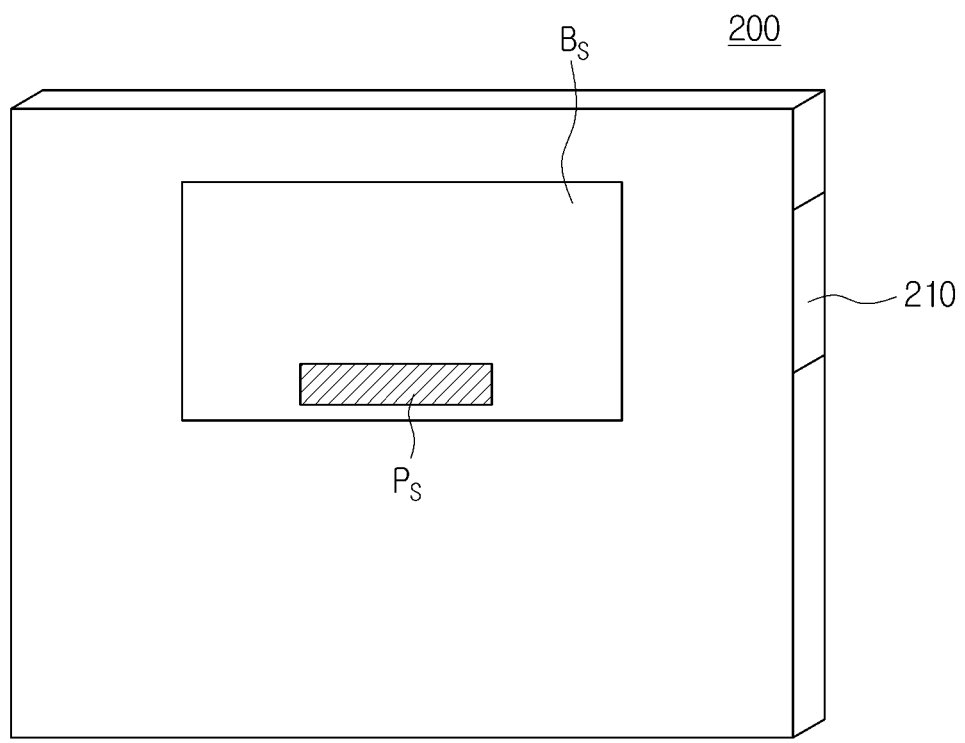

FIG. 10 illustrates a detector battery coupling unit in accordance with one embodiment, and FIGS. 11A and 11B illustrate a position of a detector battery side connection terminal in accordance with a variety of embodiments.

The detector battery (BS) may be separated from the X-ray detector 200 and then mounted to the body 110. Referring to FIG. 10, a detector battery coupling unit 113 may be provided in the body 110 to guide the detector battery (BS) so that the detector battery (BS) is coupled to the detector battery connector 340. The coupling unit 113 may be coupled to the detector battery (BS) to fix a position of the detector battery (BS) and thus the coupling unit 113 may help the detector battery side-connection terminal (PS) and the detector battery connector side-connection terminal (PM) to be stably coupled to each other.

FIG. 10 illustrates that the coupling unit 113 is disposed on a lower end portion of the handle 112, but a position of the coupling unit 113 is not limited thereto.

Otherwise, the detector battery (BS) may be mounted to the body 110 while being coupled to the X-ray detector 200. Referring to FIG. 11A, the connection terminal of the detector battery (BS) may be provided in a wired connection terminal 210 of the X-ray detector 200. As a result, when the X-ray detector 200 is connected to the body 110 through a wire, the detector battery (BS) may be connected to the body 110.

As another example, referring to FIG. 11B, other than the wired connection terminal 210 of the X-ray detector 200, the connection terminal of the detector battery (BS) coupled to the X-ray detector 200 may be exposed to the outside. In this case, in the inside of the detector accommodation unit 111 of the body 110, the detector battery connector 340 may be provided on a position to which the exposed connection terminal of the detector battery (BS) is connected when the X-ray detector 200 is accommodated.

The detector battery (BS) may supply the power to some or all of component of the body 110, as well as the brake 164. Particularly, the detector battery (BS) may supply the power to the main input/output unit 150, the controller 180, and the image processor 190 to provide an X-ray image or a control condition of the X-ray apparatus to a user.

Figure 12:
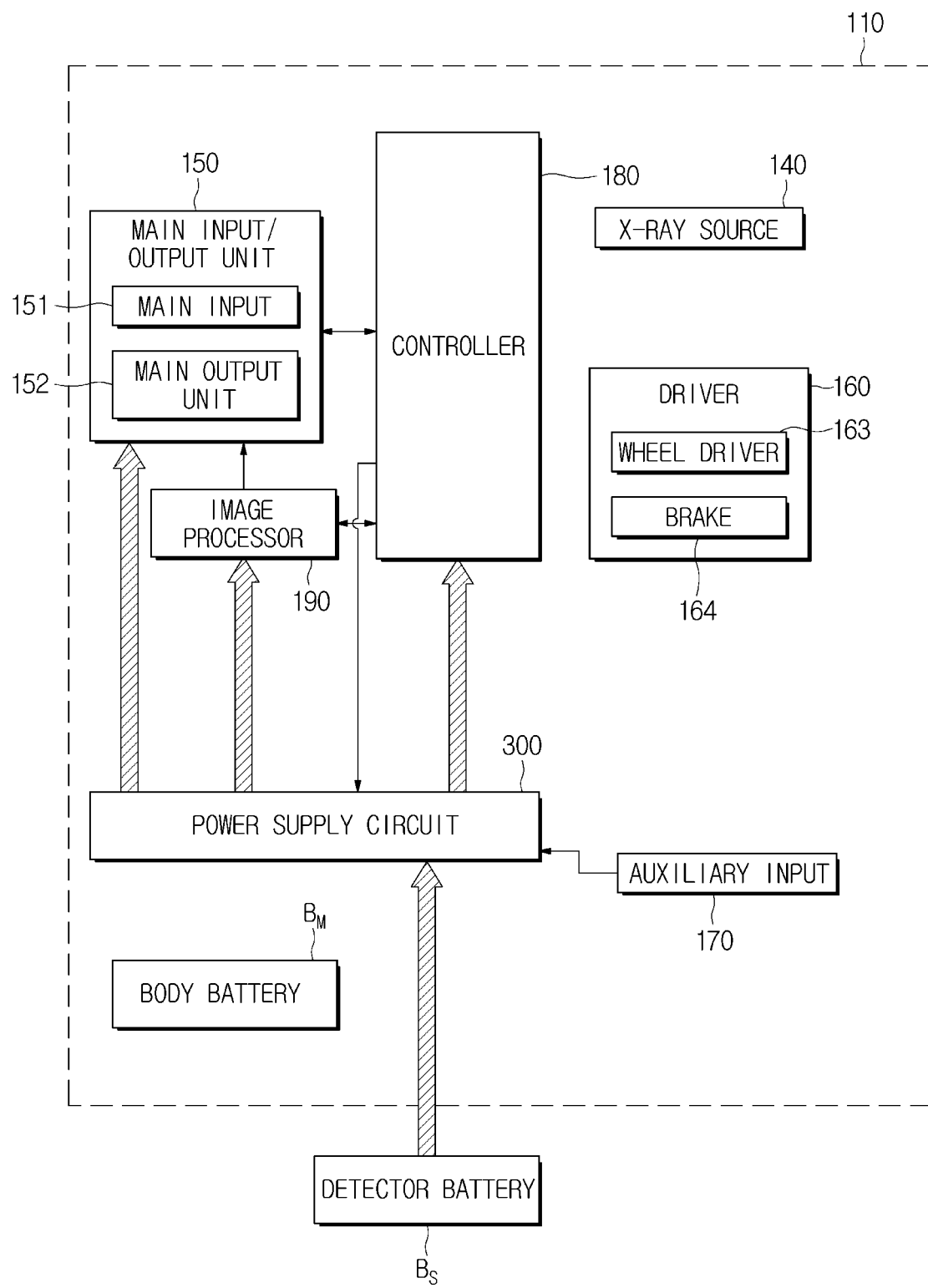
FIG. 12 illustrates a power flow when a body battery of an X-ray apparatus is incapable of supplying the power in accordance with another embodiment.

FIG. 12 illustrates a power flow when a body battery of an X-ray apparatus is incapable of supplying the power in accordance with another embodiment.

When it is impossible to supply the power of the body battery (BM) or the external commercial electricity, operating the X-ray apparatus 100 may be required other than moving the body 110. For example, the user may want to confirm an X-ray image of an object via the X-ray apparatus, after the body battery (BM) is discharged. In this case, by connecting the detector battery (BS) of the X-ray detector 200 to the body 110, a temporary power may be supplied to the main input/output unit 150, the controller 180, and the image processor 190. If the detector battery (BS) has an output of 38.76WH, the body 110 having a consumption electricity of 50W may be operated for approximately 0.8 hour.

Figure 13:
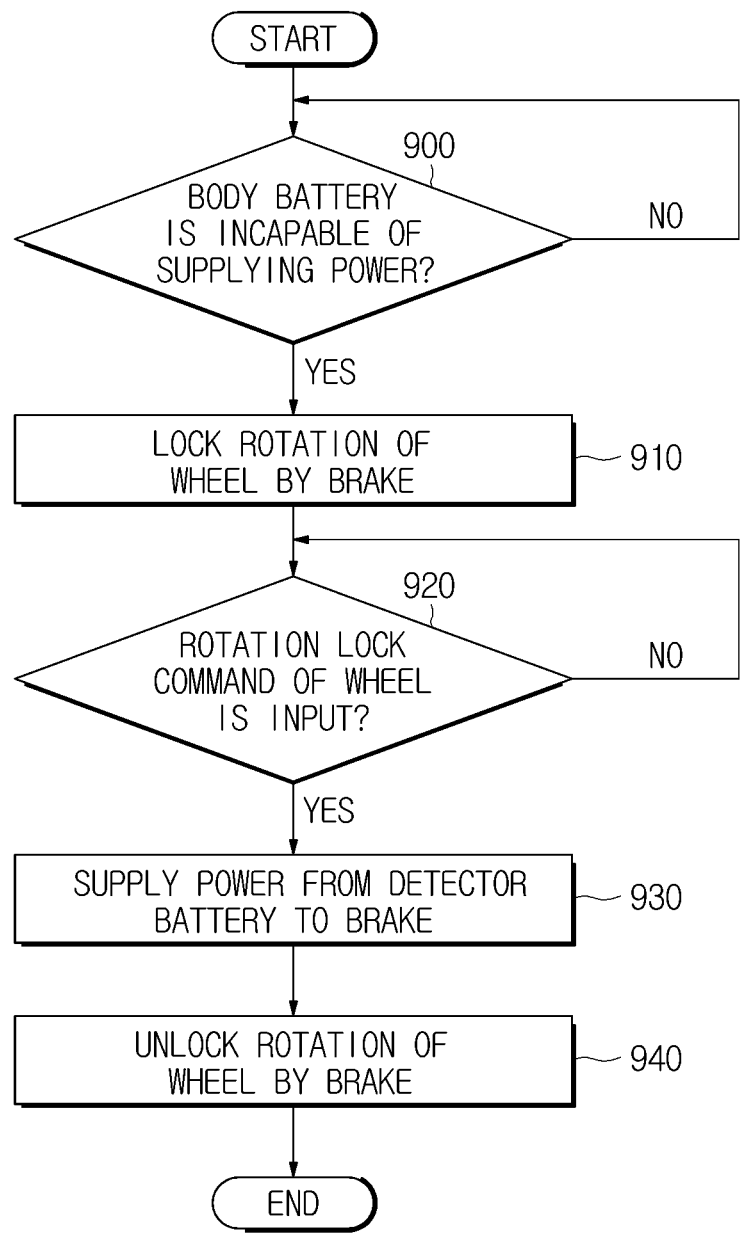
FIG. 13 illustrates a flow chart of the X-ray apparatus in accordance with one embodiment.

FIG. 13 illustrates flow chart of the X-ray apparatus in accordance with one embodiment.

Firstly, the X-ray apparatus 100 may confirm whether the body battery (BM) is in a state incapable of supplying the power (900). The state incapable of supplying the power may include a state in which the body battery (BM) is discharged and a state in which an output is blocked since the danger of the body battery (BM) is detected. When the body battery (BM) is capable of supplying the power, the X-ray apparatus 100 may confirm whether the body battery (BM) is capable of supplying the power, again.

Meanwhile, when the body battery (BM) is incapable of supplying the power, the X-ray apparatus 100 may lock the rotation of the wheel 165 via the brake 164 (910). The X-ray apparatus 100 may lock the rotation of the wheel 165 to prevent the damage of the X-ray apparatus 100 and to secure the user safety, since it is no longer possible to supply the power for the movement of the X-ray apparatus 100.

When the rotation of the wheel 165 is locked, the X-ray apparatus 100 may confirm whether the rotation lock command of the wheel 165 is input (920). In this time, the rotation lock command of the wheel 165 may be input via the auxiliary input 170. However, when the rotation lock command is not input, the X-ray apparatus 100 may repeatedly confirm whether the rotation lock command of the wheel 165 is input.

Meanwhile, when the rotation lock command is input, the X-ray apparatus 100 may supply the power from the detector battery (BS) to the brake 164 (930). As a result, the X-ray apparatus 100 may release the locked rotation of the wheel 165 by the brake 164 (940).

When the locked rotation of the wheel 165 is released, the user may rotate the wheel 165 by applying an external force to move the X-ray apparatus 100 to a desired position.

As is apparent from the above description, according to the proposed X-ray apparatus and the control method thereof, although the body battery provided in the body is discharged, it may be possible to move the X-ray apparatus by allowing the wheel to be rotatable via the power supplied from the auxiliary battery of the X-ray detector.

According to the proposed X-ray apparatus and the control method thereof, it may be possible to prevent a malfunction of the brake caused by the charging power of the auxiliary battery since the body battery charges the auxiliary battery through a charging path only when the auxiliary battery of the X-ray detector is connected to the body, during the power is supplied from the body battery provided in the body.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A mobile X-ray apparatus comprising:
   a body including a body battery, a detector accommodator provided at an outside of the body, and a wheel provided at a lower side of the body;
   an X-ray source coupled to the body and configured to emit X-rays to an object;
   a detector battery connector provided on the body and connectable to a detector battery that is mountable on an X-ray detector for detecting X-rays emitted by the X-ray source;
   a power supply circuit connected to the detector battery connector to form a first path in which a power is supplied from the body battery to the detector battery and a second path in which a power is supplied from the detector battery to the body; and
   a controller configured to control the power supply circuit to selectively form the first path and the second path.

2. The mobile X-ray apparatus of claim 1, wherein the controller controls the power supply circuit to form the first path in which a power is supplied from the body battery to the detector battery connector when the body battery is capable of supplying a power.

3. The mobile X-ray apparatus of claim 1, wherein the controller controls the power supply circuit to form the second path in which a power is supplied from the detector battery to the body when the body battery is incapable of supplying a power.

4. The mobile X-ray apparatus of claim 1, wherein the power supply circuit further comprises a detector battery recognizer configured to determine whether the detector battery is connected to the detector battery connector,
   wherein the controller controls the power supply circuit to block the first path when the detector battery is not connected to the detector battery connector.

5. The mobile X-ray apparatus of claim 1, wherein the detector battery connector is positioned at the detector accommodator provided on a surface of the outside of the body, and
   the detector battery connector is connectable to the detector battery mounted on the X-ray detector when the X-ray detector is accommodated in the detector accommodator.

6. The mobile X-ray apparatus of claim 1, wherein the detector battery connector is provided on a detector battery coupler that is provided on a lower end of a handle of the body to guide the detector battery such that the detector battery is connected to the detector battery connector.

7. The mobile X-ray apparatus of claim 1, wherein the body further comprises:
   a wheel driver configured to provide the wheel with a torque using the power supplied from the body battery; and
   a brake configured to lock a rotation of the wheel,
   wherein the controller controls the brake such that the wheel is rotatable by the power supplied from the detector battery when the rotation of the wheel is prevented.

8. The mobile X-ray apparatus of claim 7, wherein the power supply circuit comprises:
   a first converter configured to reduce a voltage of the power supplied from the body battery to the brake; and
   a second converter configured to reduce a voltage of the power supplied from the body battery to the detector battery.

9. The mobile X-ray apparatus of claim 7, wherein the power supply circuit further comprises:
   a third converter configured to increase a voltage of the power supplied from the detector battery to the brake.

10. The mobile X-ray apparatus of claim 7, wherein the power supply circuit further comprises:
    a first switch configured to form a path in which a power is supplied to the brake from one of the body battery and the detector battery.

11. The mobile X-ray apparatus of claim 7, wherein the power supply circuit further comprises:
    a second switch configured to transmit or block a power supplied to the brake.

12. The mobile X-ray apparatus of claim 9, wherein the power supply circuit further comprises:
    a third switch configured to transmit the power, a voltage of which is increased by the third converter, to the brake.

13. The mobile X-ray apparatus of claim 8, wherein the power supply circuit further comprises:
    a fourth switch configured to transmit the power, a voltage of which is reduced by the first converter, to the brake.

14. A mobile X-ray apparatus comprising:
    a body including a body battery, a detector accommodator provided at an outside of the body, and a wheel provided at a lower side of the body;
    an X-ray source coupled to the body and configured to emit X-rays to an object;
    a detector battery connector provided on the body and connectable to a detector battery that is mountable on an X-ray detector for detecting X-rays emitted by the X-ray source;
    a power supply circuit connected to the detector battery connector to form a first path in which a power is supplied from the body battery to the detector battery and a second path in which a power is supplied from the detector battery to the body;
    a controller configured to control the power supply circuit to selectively form the first path and the second path; and
    an auxiliary input configured to receive a rotation unlock command of the wheel,
    wherein the controller controls the power supply circuit to form the second path along which a power is supplied from the detector battery to the body when the rotation unlock command is received through the auxiliary input.

15. The mobile X-ray apparatus of claim 14, wherein the body further comprises:
    a wheel driver configured to provide the wheel with a torque using the power supplied from the body battery and a brake configured to lock a rotation of the wheel,
    wherein the controller controls the brake such that the wheel is rotatable by the power supplied from the detector battery when the rotation unlock command is received.

16. The mobile X-ray apparatus of claim 14, wherein the auxiliary input is provided on a handle provided on the body.

17. A method of controlling a mobile X-ray apparatus, the method comprising:
    locking a rotation of a wheel provided on a body when a body battery provided on the body of the mobile X-ray apparatus is incapable of supplying a power;
    receiving a power control command of the mobile X-ray apparatus; and
    in response to receiving the power control command, forming a second path in which a power is supplied to the body from a detector battery that is connectable to a detector battery connector of the body.

18. The method of claim 17, further comprising: forming a first path in which a power is supplied from the body battery to the detector battery when the body battery is capable of supplying a power.

19. The method of claim 17, wherein:
    the receiving of the power control command comprises receiving a rotation unlock command of the wheel through an auxiliary input that is provided on the body, and
    the forming of the second path comprises, in response to receiving the rotation unlock command of the wheel, forming a power supply path in which a power of the detector battery is supplied to a brake provided on the body such that the wheel is rotatable.

20. The method of claim 19, further comprising supplying a power of the detector battery to the brake.

* * * * *